US010272080B2

(12) United States Patent
Bhide et al.

(10) Patent No.: US 10,272,080 B2
(45) Date of Patent: Apr. 30, 2019

(54) SELECTIVE DOPAMINE D4 RECEPTOR AGONISTS FOR TREATMENT OF WORKING MEMORY DEFICITS

(71) Applicants: Florida State University Research Foundation, Inc., Tallahassee, FL (US); The General Hospital Corporation, Boston, MA (US)

(72) Inventors: Pradeep G. Bhide, Tallahassee, FL (US); Jinmin Zhu, Tallahassee, FL (US); Joseph Biederman, Brookline, MA (US); Thomas J. Spencer, Carlisle, MA (US)

(73) Assignees: Florida State University Research Foundation, Inc., Tallahassee, FL (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/021,304

(22) PCT Filed: Sep. 12, 2014

(86) PCT No.: PCT/IB2014/064470
§ 371 (c)(1),
(2) Date: Mar. 11, 2016

(87) PCT Pub. No.: WO2015/036972
PCT Pub. Date: Mar. 19, 2015

(65) Prior Publication Data

US 2016/0220563 A1 Aug. 4, 2016

Related U.S. Application Data

(60) Provisional application No. 61/877,417, filed on Sep. 13, 2013.

(51) Int. Cl.

| | |
|---|---|
| ***A61P 25/28*** | (2006.01) |
| ***A61K 9/00*** | (2006.01) |
| ***A61K 9/06*** | (2006.01) |
| ***A61K 9/08*** | (2006.01) |
| ***A61K 9/14*** | (2006.01) |
| ***A61K 9/20*** | (2006.01) |
| ***A61K 9/48*** | (2006.01) |
| ***A61K 31/495*** | (2006.01) |
| ***A61K 31/4545*** | (2006.01) |

(52) U.S. Cl.
CPC .......... *A61K 31/495* (2013.01); *A61K 9/0019* (2013.01); *A61K 9/0053* (2013.01); *A61K 9/06* (2013.01); *A61K 9/08* (2013.01); *A61K 9/14* (2013.01); *A61K 9/20* (2013.01); *A61K 9/48* (2013.01); *A61K 9/4825* (2013.01); *A61K 31/4545* (2013.01); *A61P 25/28* (2018.01)

(58) Field of Classification Search
CPC ............................ A61K 31/495; A61P 25/28
USPC .................................................... 514/255.03
See application file for complete search history.

(56) References Cited

U.S. PATENT DOCUMENTS 8,258,139 B2 9/2012 Ikeda et al.

FOREIGN PATENT DOCUMENTS

| | | |
|---|---|---|
| EP | 2010505 B1 | 12/2012 |
| WO | 2007110868 A2 | 10/2007 |

OTHER PUBLICATIONS

Sood et al., "PD168077, a D4 receptor agonist, reverses object recognition deficits in rats: potential role for D4 receptor mechanisms in improving cognitive dysfunction in schizophrenia", Journal of Psychopharmacology, vol. 25, No. 6, pp. 792-800 (2011).*
Goldman-Rakic PS (1995) Cellular basis of working memory. Neuron 14:477-485.
Goldman-Rakic PS (1996) Regional and cellular fractionation of working memory. Proc Natl Acad Sci U S A 93:13473-13480.
Goldman-Rakic PS (1999) The "psychic" neuron of the cerebral cortex. Ann N Y Acad Sci 868:13-26.
Park S, Holzman PS, Goldman-Rakic PS (1995) Spatial working memory deficits in the relatives of schizophrenic patients. Arch Gen Psychiatry 52:821-828.
Arnsten AF (2011) Prefrontal cortical network connections: key site of vulnerability in stress and schizophrenia. Int J Dev Neurosci 29:215-223.
Wang M, Gamo NJ, Yang Y, Jin Le, Wang XJ, Laubach M, Mazer JA, Lee D, Arnsten AF (2011) Neuronal basis of age-related working memory decline. Nature 476:210-213.
Alderson RM, Kasper LJ, Hudec KL, Patros CH (2013) Attention-deficit/hyperactivity disorder (ADHD) and working memory in adults: a meta-analytic review. Neuropsychology 27:287-302.
Zhang K, Grady CJ, Tsapakis EM, Andersen SL, Tarazi FI, Baldessarini RJ (2004) Regulation of working memory by dopamine D4 receptor in rats. Neuropsychopharmacology 29:1648-1655.
Robbins TW, Amsten AF (2009) The neuropsychopharmacology of fronto-executive function: monoaminergic modulation. Annu Rev Neurosci 32:267-287.
Faraone SV, Biederman J (1998) Neurobiology of attention-deficit hyperactivity disorder. Biol Psychiatry 44:951-958.
Lasky-Su J, Lange C, Biederman J, Tsuang M, Doyle AE, Smaller JW, Laird N, Faraone S (2008) Family-based association analysis of a statistically derived quantitative traits for ADHD reveal an association in DRD4 with inattentive symptoms in ADHD individuals. Am J Med Genet B Neuropsychiatr Genet 147B:100-106.

(Continued)

*Primary Examiner* — Kevin E Weddington
(74) *Attorney, Agent, or Firm* — Christopher M. Ramsey; GrayRobinson, P.A.

(57) ABSTRACT

Working memory deficits are treated and working memory is improved with a composition that comprises a therapeutically effective amount of one or more respective selective dopamine D4 receptor agonists and/or pharmaceutically acceptable analogs, salts or hydrates of the respective one or more selective dopamine D4 receptor agonists. This composition can be administered to a subject to improve the subject's working memory.

16 Claims, 10 Drawing Sheets

(56) References Cited

OTHER PUBLICATIONS

Monuteaux MC, Seidman LJ, Faraone SV, Makris N, Spencer T, Valera E, Brown A, Bush G, Doyle AE, Hughes S, Helliesen M, Mick E, Biederman J (2008) A preliminary study of dopamine D4 receptor genotype and structural brain alterations in adults with ADHD. Am J Med Genet B Neuropsychiatr Genet 147B:1436-1441.

Zhu J, Lee KP, Spencer TJ, Biederman J, Bhide PG (2014) Transgenerational transmission of hyperactivity in a mouse model of ADHD. J Neurosci 34:2768-2773.

Zhu J, Zhang X, Xu Y, Spencer TJ, Biederman J, Bhide PG (2012) Prenatal nicotine exposure mouse model showing hyperactivity, reduced cingulate cortex volume, reduced dopamine turnover, and responsiveness to oral methylphenidate treatment. The Journal of neuroscience : the official journal of the Society for Neuroscience 32:9410-9418.

Bissonette GB, Powell EM, Roesch MR (2013) Neural structures underlying set-shifting: roles of medial prefrontal cortex and anterior cingulate cortex. Behav Brain Res 250:91-101.

Bissonette GB, Bae MH, Suresh T, Jaffe DE, Powell EM (2014) Prefrontal cognitive deficits in mice with altered aerebral cortical GABAergic interneurons. Behav Brain Res 259:143-151.

Zhu J, Spencer TJ, Liu-Chen LY, Biederman J, Bhide PG (2011) Methylphenidate and mu opioid receptor interactions: a pharmacological target for prevention of stimulant abuse. Neuropharmacology 61:283-292.

Balcioglu A, Ren JQ, McCarthy D, Spencer TJ, Biederman J, Bhide PG (2009) Plasma and brain concentrations of oral therapeutic doses of methylphenidate and their impact on brain monoamine content in mice. Neuropharmacology 57:687-693.

Browman, et al., "A-412997, a selective dopamine D4 agonist, improves cognitive performance in rats". Pharmacology, Biochemistry and Behavior, 2005, vol. 82, No. 1, pp. 148-155.

Furth, et al., "Dopamine, cognitive function, and gamma oscillations: role of D4 receptors", Frontiers in Cellular Neuroscience, Jul. 2, 2013, vol. 7, Article No. 102, pp. 1-19.

Sanna et al., Dopamine D2-like receptor agonists Induce penile erection in male rats: differential role of D2, D3 and D4 receptors in the paraventricular nucleus of the hypothalamus. Behavioural Brain Research, 2011, vol. 225, No. 1, pp. 169-176.

International Search Report and Written Opinion dated Feb. 27, 2015 in corresponding International Patent Application No. PCT/IB2014/64470.

* cited by examiner

PD-168,077

A-412,997

SELECTIVE DOPAMINE D4 RECEPTOR AGONISTS FOR TREATMENT OF WORKING MEMORY DEFICITS

CROSS-REFERENCE TO RELATED APPLICATIONS

This application claims benefit of priority of International Application No. PCT/IB2014/064470, entitled, "SELECTIVE DOPAMINE D4 RECEPTOR AGONISTS FOR TREATMENT OF WORKING MEMORY DEFICITS" filed Sep. 12, 2014, which in turn claims priority to U.S. Provisional Patent Application No. 61/877,417, entitled "SELECTIVE DOPAMINE D4 RECEPTOR AGONISTS FOR TREATMENT OF WORKING MEMORY DEFICITS" filed Sep. 13, 2013. The entire contents and disclosures of these patent applications are incorporated herein by reference in their entirety.

This application makes reference to U.S. Provisional Patent Application No. 61/716,769, entitled "NOVEL CLASS OF NON-STIMULANT TREATMENT FOR ADHD AND RELATED DISORDERS," filed Oct. 22, 2012. U.S. patent application Ser. No. 14/027,676, entitled "NOVEL CLASS OF NON-STIMULANT TREATMENT AND ADHD AND RELATED DISORDERS," filed Sep. 16, 2013. The entire contents and disclosures of these patent applications are incorporated herein by reference.

GOVERNMENT INTEREST STATEMENT

This invention was made with the United States government support under Grant Nos. R01DA020796 and R21DA027358 awarded by the National Institutes of Health. The government has certain rights in the invention.

BACKGROUND

Field of the Invention

The present invention relates generally to the treatment of memory-related diseases deficits.

Related Art

Working memory capacity is the ability to retain and manipulate information over short periods of time. Impaired working memory is a key feature of cognitive dysfunctions in multiple conditions including attention deficit/hyperactivity disorder (ADHD), bipolar disorder, schizophrenia, Alzheimer's disease and Parkinson's disease, etc.

SUMMARY

According to a first broad aspect, the present invention provides a method comprising: administering a composition that comprises a therapeutically effective amount of one or more respective selective dopamine D4 receptor agonists, and/or pharmaceutically acceptable analogs, salts or hydrates of the one or more respective selective dopamine D4 receptor agonists to a subject to improve working memory in the subject.

According to a second broad aspect, the present invention provides a pharmaceutical composition comprising a therapeutically effective amount of one or more respective selective dopamine D4 receptor agonists and/or pharmaceutically acceptable analogs, salts or hydrates of the one or more respective selective dopamine D4 receptor agonists as an active ingredient in a formulation aimed at improving working memory of a subject via an administration of the pharmaceutical composition to the subject.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
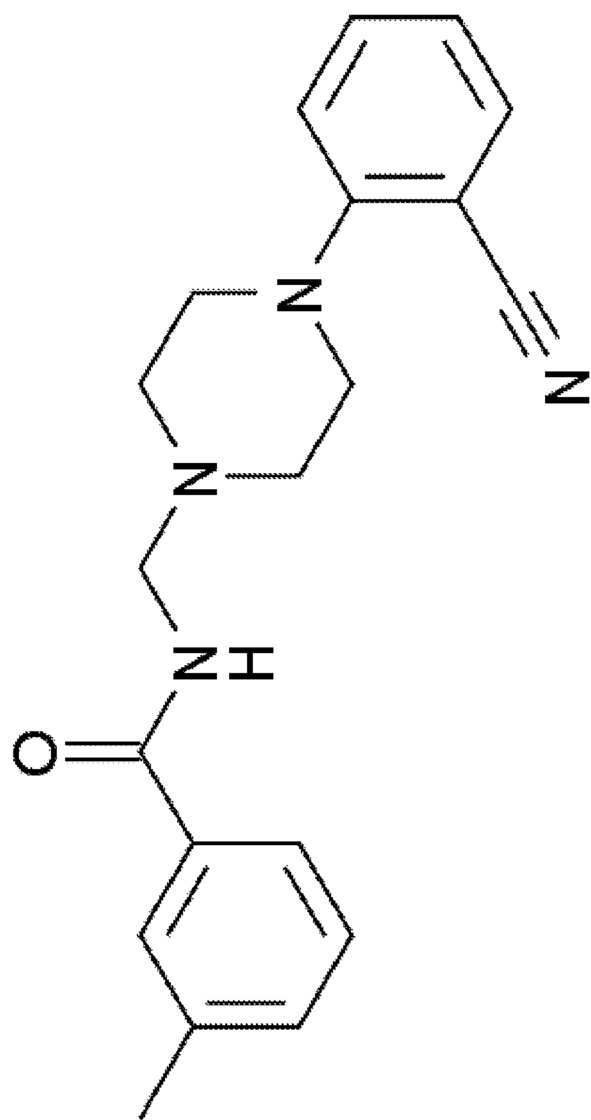
FIG. 1 shows the structure of a selective D4 receptor agonist PD 168077.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purpose of the present invention, the term "active ingredient" is the substance in a pharmaceutical drug that is biologically active. It can be also called "active pharmaceutical ingredient." Some medication products may contain one or more active ingredient.

For purpose of the present invention, the term "additive" refers to a substance added to another in relatively small amounts to effect a desired change in properties. In foods, an additive may be any of various chemical substances added to produce desirable effects. Additives include substances such as artificial or natural colorings and flavorings; stabilizers, emulsifiers, and thickeners; preservatives and humectants (moisture-retainers); and supplementary nutrients, etc. For example, an additive in drinking water could be sugar, saccharin, salt, etc.

For purposes of the present invention, the term "administration in conjunction with" refers to administering respective formulations sequentially, separately and/or simultaneously, over the course of treatment of the relevant condition, which condition may be acute or chronic. In some embodiments, two formulations are administered (possibly repeatedly) sufficiently closely in time for there to be a beneficial effect for the subject, that is greater, over the course of the treatment of the relevant condition, than if either of the two formulations are administered (optionally repeatedly) alone, in the absence of the other formulation, over the same course of treatment. Determination of whether a combination provides a greater beneficial effect in respect off and over the course of treatment of, a particular condition, will depend upon the condition to be treated or prevented, but may be achieved routinely by the person skilled in the art. Thus, the term "in conjunction with" includes that one or other of the two formulations may be administered (optionally repeatedly) prior to, after, and/or at the same time as, administration with the other component. When used in this context, the terms "administered simultaneously" and "administered at the same time as" include the possibility that individual doses are administered, for example, within 48 hours, 24 hours, 18 hours, 12 hours, 6 hours, 3 hours, 2 hours, 1 hour, or 30 minutes of each other. The dose of the composition to be administered may depend on the relevant indication, the age, weight and sex of the subject. The dose of the composition to be administered may be determined by a physician. In one embodiment, the dosage is in a range of from 0.001 mg/kg to 10 mg/kg. The typical daily dose of the active ingredients varies within a broad range and may depend on various factors such as the relevant indication, the route of administration, the age, weight and sex of the subject and may be determined by a physician. In some embodiments, oral and parenteral dosages may be in the range of 0.1 to 2,000 mg per day of total active ingredients.

For purpose of the present invention, the term "agonism" refers to biological action of a substance upon a receptor which ultimately produces the same effects on the receptor as the effects of another substance, rendering both the substances agonists of the same receptor.

For purpose of the present invention, the term "agonist" refers to a compound that binds to a receptor and activates the receptor signaling mechanisms to produce a biological response.

For purpose of the present invention, the term "analogue" and the term "analog" refer to one of a group of chemical compounds that share structural and/or functional similarities but are different in respect to elemental composition. A structural analog is a compound having a structure similar to that of another one, but differing from it in respect of one or more components, such as one or more atoms, functional groups, or substructures, etc. Functional analogs are compounds that have similar physical, chemical, biochemical, or pharmacological properties. Functional analogs are not necessarily also structural analogs with a similar chemical structure.

For purpose of the present invention, the term "antagonist" refers to a compound that binds to a receptor and blocks or disrupts the action of an agonist at the receptor.

For purposes of the present invention, the term "Attention Deficit/Hyperactivity Disorder (ADHD)" refers to conditions such as ADHD, ADHD NOS, Hyperkinetic Disorder, Attention Deficit Disorder with and without Hyperactivity, and others, as defined by DSM III, DSM III-R, DSM IV, DSM IV-TR, DSM V, future DSM definitions, ICD 8, ICD 9, ICD 10 and future versions of ICD as well as similar definitions of ADHD. For purposes of the present invention, the term "ADHD" includes both full and subthreshold conditions where there are not sufficient ADHD symptoms to meet full diagnostic criteria, late onset of ADHD symptoms and ADHD symptoms that occur in the context of comorbid disorders, after head trauma or due to unknown etiology.

For purpose of the present invention, the term "capsule" refers to a gelatinous envelope enclosing the active substance. Capsules can be designed to remain intact for some hours after ingestion in order to delay absorption. They may also contain a mixture of slow- and fast-release particles to produce rapid and sustained absorption in the same dose.

For purpose of the present invention, the term "cognitive deficit" and the term "cognitive impairment" refer to any characteristic that acts as a barrier to the cognition process. Cognitive deficits may occur as a result of normal aging, may be congenital or caused by environmental factors such as brain injuries, neurological disorders, or mental illness.

For purpose of the present invention, the term "combination" and the term "combination preparation" refer to both true combinations, meaning medicaments physically combined in one preparation such as a tablet or injection fluid, as well as a "kit-of-parts" comprising medicaments in separate dosage forms, together with instructions for use, optionally with further means for facilitating compliance with the administration of the component compounds, e.g., label or drawings. With true combinations, the pharmacotherapy by definition is simultaneous. The contents of "kit-of-parts" may be administered either simultaneously or at different time intervals. Therapy being either concomitant or sequential may be dependent on the characteristics of the other medicaments used, characteristics like onset and duration of action, plasma levels, clearance, etc., as well as on the disease, the stage of the disease, and characteristics of the individual subject.

For purpose of the present invention, the term "comprising", the term "having", the term "including," and variations of these words are intended to be open-ended and mean that there may be additional elements other than the listed elements.

For purposes of the present invention, the term "daily dose" refers to the total dosage amount administered to an individual in a single 24-hour day.

For purpose of the present, the term "delayed release" refers to oral medicines that do not immediately disintegrate and release the active ingredient(s) into the body. For example, an enteric coated oral medication dissolves in the intestines rather than the stomach.

For purposes of the present invention, the term "dietary supplement" refers to a product taken by mouth that contains a "dietary ingredient" intended to supplement the diet. The "dietary ingredients" in these products may include: vitamins, minerals, herbs or other botanicals, amino acids, and substances such as enzymes and metabolites. Dietary supplements may also be extracts or concentrates, and may be found in many forms such as tablets, capsules, softgels, gelcaps, liquids, or powders. Dietary supplements may also be in other forms, such as a bar, but if they are, information on the label of the dietary supplement may not represent the product as a conventional food or a sole item of a meal or diet. For purpose of the present invention, the term "dopamine anta".

gonist" or the term "dopamine receptor antagonist" refers to one of a group of compounds that block or inhibit the binding of dopamine to dopamine receptors. Dopamine is a neurotransmitter that is found in the brains of animals, including humans, and is essential for proper nerve signal transmission.

For purposes of the present invention, the term "dose" refers to a specified amount of medication taken at one time.

For purpose of the present invention, the term "dosage" refers to the administering of a specific amount, number, and frequency of doses over a specified period of time. Dosage implies duration. A "dosage regimen" is a treatment plan for administering a drug over a period of time.

For purposes of the present invention, the term "effective amount" or "effective dose" or grammatical variations thereof refers to an amount of an agent sufficient to produce one or more desired effects. The effective amount may be determined by a person skilled in the art using the guidance provided herein.

For purposes of the present invention, the terms "improve," "improving" or "improvement" or grammatical variations thereof used in relation to cognitive functions refer to the ability to achieve a measurable increase in performance in relation to tasks used to test these cognitive functions in humans.

For purposes of the present invention, the term "medical therapy" refers to prophylactic, diagnostic and therapeutic regimens carried out in vivo or ex vivo on humans or other mammals.

For purposes of the present invention, the term "memory" refers to the biological processes in which information is encoded, stored, and retrieved. Encoding is the first stage which includes receiving, processing and combining of received information. Storage is the second stage which includes a creation of a record of the encoded information. Retrieval is the third stage which involves recall or recollection the stored information in response to some cue for use in a process or activity.

For purposes of the present invention, the term "mg/kg" refers to the dose of a substance administered to an individual in milligrams per kilogram of body weight of the individual.

For purposes of the present invention, the term "nutraceutical" refers to compounds and compositions that are useful in both the nutritional and pharmaceutical field of application. Thus, nutraceutical compositions of the present invention may be used as supplement to food and beverages, and as pharmaceutical formulations for enteral or parenteral application which may be solid formulations such as capsules or tablets, or liquid formulations, such as solutions or suspensions. In some embodiments of the present invention, nutraceutical compositions may also comprise food and beverages containing therapeutically effective amount of one or more respective selective dopamine D4 receptor agonists and/or pharmaceutically acceptable analogs, salts or hydrates of the one or more respective selective dopamine D4 receptor agonists, as well as supplement compositions, for example dietary supplements.

For purposes of the present invention, the term "parenteral route" refers to the administration of a composition, such as a drug in a manner other than through the digestive tract. Parenteral routes include routes such as intravenous, intra-arterial, transdermal, intranasal, sub-lingual and intraosseous, etc. For example, intravenous is also known as I.V., which is giving directly into a vein with injection. As the drug directly goes into the systemic circulation, it reaches the site of action resulting in the onset the action.

For purposes of the present invention, the term "pharmaceutically acceptable" refers to a compound or drug approved or approvable by a regulatory agency of a federal or a state government, listed or listable in the U.S. Pharmacopeia or in other generally recognized pharmacopeia for use in mammals, including humans.

For purposes of the present invention, the term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They may be prepared in situ when finally isolating and purifying the compounds of the invention, or separately by reacting them with pharmaceutically acceptable non-toxic bases or acids, including inorganic or organic bases and inorganic or organic acids. Pharmaceutically acceptable salts may be obtained using standard procedures well known in the art, for example by mixing a compound of the present invention with a suitable acid, for instance an inorganic acid or an organic acid.

For purpose of the present invention, the term "pharmaceutical composition" refers to a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. A pharmaceutical composition includes enough of the active object compound to produce the desired effect upon the progress or condition of diseases. Accordingly, a pharmaceutical composition encompasses any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof, i.e., the subject.

For purpose of the present invention, the term "pharmaceutical formulation" and the term "drug formulation" refer to a mixtures or a structure in which different chemical substances, including the active drug, are combined to form a final medicinal product, such as a sterile product, a capsule, a tablet, a powder, a granule, a solution, an emulsion, a topical preparation, a non-conventional product such as semi-solid or sustained-release preparations, liquid, etc. Pharmaceutical formulation is prepared according to a specific procedure, a "formula." The drug formed varies by the route of administration. For example, oral drugs are normally taken as tablet or capsules.

For purpose of the present invention, the term "selective dopamine D4 receptor agonist" and the term "selective D4R agonist" refer to a compound that selectively targets or binds the D4 subtype of dopamine receptors and triggers or improves the activity of the D4 receptor. In embodiments of the present invention, compounds that act as selective dopamine D4 receptor agonists encompass PD 168077, ABT-724, ABT-670, F-15063, A-412997, FAUC-327, Ro-10-5824, CP-226269, PIP-3EA, FAUC-299, FAUC-316, FAUC-179, FAUC-356, FAUC-312, A-369508, etc., and pharmaceutically acceptable analogs or salts thereof.

For purposes of the present invention, the term "subject" refers to an animal, for example, a mammal, such as a human, who has been the object of treatment, observation or experiment.

For purpose of the present invention, the term "tablet" refers to a pharmaceutical dosing form. A tablet comprises a mixture of active substances and excipients, usually in powder form, pressed or compacted from a powder into a solid dose. The excipients can include diluents, binders or granulating agents, glidants and lubricants to ensure efficient tableting; disintegrants to promote tablet break-up in the digestive tract; sweeteners or flavors to enhance taste; and pigments to make the tablets visually attractive. A polymer coating is often applied to make the tablet smoother and easier to swallow, to control the release rate of the active ingredient, to make it more resistant to the environment (extending its shelf life), or to enhance the tablet's appearance. The disintegration time can be modified for a rapid effect or for sustained release. For example, some tablets are designed with an osmotically active core, surrounded by an impermeable membrane with a pore in it. This allows the drug to percolate out from the tablet at a constant rate as the tablet moves through the digestive tract. Tablets can also be coated with sugar, varnish, or wax to disguise the taste.

For purposes of the present invention, the term "therapeutically effective amount" refers to the amount of a compound or composition that, when administered to a subject for treating a disease or disorder, or at least one of the clinical symptoms of a disease or disorder, is sufficient to affect such treatment of the disease, disorder, or symptom. A "therapeutically effective amount" may vary depending, for example, on the compound, the disease, disorder, and/or symptoms of the disease or disorder, severity of the disease, disorder, and/or symptoms of the disease or disorder, the age, weight, and/or health of the subject to be treated, and the judgment of the prescribing physician. An appropriate amount in any given instance may be readily ascertained by those skilled in the art or capable of determination by routine experimentation.

For purposes of the present invention, the term "treating" or the term "treatment" of any disease or disorder refers to arresting or ameliorating a naturally occurring condition (for example, as a result of aging), disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to slowing the progression of a condition, inhibiting the disease or disorder, either physically, (e.g., stabilization of a discernible symptom), physiologically, (e.g., stabilization of a physical parameter), or both, and to inhibiting or slowing the progression of at least one physical parameter which may or may not be discernible to the subject. In some embodiments of the present invention, the terms "treating" and "treatment" refer to delaying the onset of the progression of the disease or disorder or at least one or more symptoms thereof in a subject who may be exposed to or predisposed to a disease or disorder even though that subject does not yet experience or display symptoms of the disease or disorder. The term "treatment" as used herein also refers to any treatment of a subject, such as a human condition or disease, and includes: (1) inhibiting the disease or condition, i.e., arresting the development or progression of the disease or condition, (2) relieving the disease or condition, i.e., causing the condition to regress, (3) stopping the symptoms of the disease, and/or (4) enhancing the conditions desired.

For purposes of the present invention, the term "working memory" refers to the biological processes of the brain that enable storage and recall of information over short periods of time. "Working memory" may include a combination of processes of the brain that provide temporary storage and manipulation of information necessary to perform complex cognitive tasks such as learning and reasoning. In other words, "working memory" refers to the system that actively holds multiple pieces of transitory information in the mind, where they may be manipulated. A subject's working memory includes subsystems that store and manipulate visual images or verbal information, as well as a central executive that coordinates these subsystems. It includes visual representation of the possible moves, and awareness of the flow of information into and out of memory, all stored for a limited amount of time. Working memory tasks require monitoring (i.e., manipulation of information or behaviors) as part of completing goal-directed actions in the setting of interfering processes and distractions. Working memory is a theoretical concept central both to cognitive psychology and neuroscience. Theories exist both regarding the theoretical structure of working memory and the role of specific parts of the brain involved in working memory. Research identifies the frontal cortex, parietal cortex, anterior cingulate, and parts of the basal ganglia as crucial.

For purposes of the present invention, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

For purposes of the present invention, a value or property is "based" on a particular value, property, the satisfaction of a condition or other factor if that value is derived by performing a mathematical calculation or logical operation using that value, property or other factor.

Description

Embodiments of the present invention provide drugs that selectively activate the dopamine D4 receptors to be used for treating working memory deficits or for improving working memory. Drugs described in some embodiments of the present invention encompass a class of compounds bearing the pharmacological action of selective dopamine D4 receptor agonism.

Working memory is a mechanism for short-term information storage, i.e., for holding information over short periods of time so that it may be accessed, manipulated and effectively utilized.[1,2,3] Working memory shows significant correlations with a range of neuropsychological functions, including visual orientation, visual retention, memory for objects, memory for faces, executive function, simple motor and complex sensorimotor function.

Impaired working memory negatively influences attention, inhibition of irrelevant stimuli, recognition of priority patterns, ability to recognize hierarchies and the meaning of stimuli (analysis and synthesis). Impaired working memory is a key feature of cognitive dysfunctions in multiple conditions including attention deficit/hyperactivity disorder (ADHD), bipolar disorder, schizophrenia, Alzheimer's disease, and Parkinson's disease.[4-7] Compelling evidence from the scientific literature suggests an involvement of the neurotransmitter dopamine in the regulation of working memory under physiological conditions.[8,9] Interestingly, working memory deficits occur in neuropsychiatric conditions that also involve dopamine imbalance, suggesting that working memory deficits may be associated with impaired dopamine function.

Dopamine is a neurotransmitter that is found in the brains of animals, including humans, and is essential for proper nerve signal transmission. The neurotransmitter dopamine is the primary endogenous ligand for dopamine receptors. Dopamine receptors are a class of G protein-coupled receptors that are prominent in the vertebrate central nervous system (CNS). There are at least five subtypes of dopamine receptors, D1, D2, D3, D4, and D5. The D1 and D5 receptors are members of the D1-like family of dopamine receptors, whereas the D2, D3 and D4 receptors are members of the D2-like family. Each of the subtypes has different distributions on neurons in brain regions thereby conferring specificity to brain functions that are mediated by dopamine. For example, D2 subtype receptors are located both in the limbic region of the brain, which is associated with cognition and emotional function, and in the striatum, which is associated with motor function. D4 receptors are found in higher concentrations in the frontal cortex and hippocampus, brain regions associated with cognitive and emotional functions including working memory function.

It is suggested that impaired dopamine D4 receptor (D4R) function is associated with ADHD and that ADHD symptoms include working memory deficits.[10,11,12] Stimulant compounds such as methylphenidate, which increase extracellular dopamine levels in the frontal cortex by the blockade of the dopamine and noradrenaline transporters, are partially efficacious in the alleviation of working memory deficits in ADHD. However, based on a study of humans with ADHD, the effect of methylphenidate on working memory is discovered to be significantly less robust than the effect of methylphenidate on core ADHD symptoms (attention, impulsivity, hyperactivity). Since methylphenidate-induced increases in dopamine can activate all of the dopamine receptor subtypes, the elevation of extracellular dopamine levels produced by the stimulant compounds is non-specific at the level of the dopamine receptor. However, such global dopamine increases would activate the D4 receptor (along with the other receptors), and would compensate for the reduced baseline activity of the D4 receptor in the frontal cortex of ADHD patient thereby effecting improvements in working memory. At the same time, activation of the other subtypes of dopamine receptors could diminish the potency of the effects of the selective activation of the D4 receptor on working memory.

Further study in a prenatal nicotine exposure mouse model with working memory deficits discloses that activity and expression of the D4R are significantly decreased in the frontal cortex of this model. Data show that although dopamine D2 receptor expression and activity are also decreased in the frontal cortex of this model, improvements in working memory produced by administration of methylphenidate, a stimulant compound, are accompanied by increase in the activity of only the D4R and not the D2 receptor. It is then believed that selective increase in frontal cortical D4R activity is associated with improvement of deficient working memory. Whereas psycho-stimulants are known to be effective in the treatment of ADHD, a disorder involving working memory deficits, these drugs do not selectively target the D4R nor working memory. Thus, stimulant compounds are inefficient drugs for treating working memory deficits. On the other hand, selective D4 receptor agonists are believed to be more potent treatments because they directly target the molecular substrate underlying the working memory deficit namely the D4 receptor.

At least some embodiments of the present invention are based, at least in part, on the above discovery that working memory deficits are associated with selective reductions in dopamine D4 receptor (D4R) activity and/or expression in the frontal cortex.

Accordingly, one embodiment of the present invention provides a method for treatment of working memory deficits or improvement of working memory in a subject by administering compounds that selectively target the dopamine D4 receptors and improve their functions.

According to some embodiments of the present invention, a composition administered to a subject comprises a therapeutically effective amount of one or more respective selective dopamine D4 receptor agonists and/or pharmaceutically acceptable analogs, salts or hydrates of the one or more respective selective dopamine D4 receptor agonists. The use of a therapeutically effective amount of one or more respective selective dopamine D4 receptor agonists and/or pharmaceutically acceptable analogs, salts or hydrates of the respective one or more selective dopamine D4 receptor agonists allows such drugs to effectively activate D4R alone and therefore improve working memory.

In one embodiment of the present invention, a treatment is performed to a subject with cognitive disorders. Treatments in embodiments of the present invention may be also provided to a subject having memory impairment regardless of the underlying etiology. A therapeutically effective amount of one or more selective dopamine D4 receptor agonists and/or pharmaceutically acceptable analogs, salts or hydrates of the one or more respective selective dopamine D4 receptor agonists may be administered to a subject having working memory deficit, which working memory deficit may be a deficit acquired before or after birth. Working memory deficits acquired before birth encompass working memory deficits induced by prenatal nicotine exposure or any other unknown reason. Working memory deficits acquired after birth encompass those working memory deficits acquired after traumas or other kinds of brain injuries, and/or developed during the process of normal aging, or associated with certain illnesses such as Alzheimer's disease or Parkinson's disease, etc. The working memory deficits may also be acquired from environmental causation such as stress, etc.

According to some embodiments of the present invention, a pharmaceutical composition comprising a therapeutically effective amount of one or more compounds that selectively target D4R is administered to a subject after acquired working memory deficit occurs. In some situations, a pharmaceutical composition comprising a therapeutically effective amount of one or more compounds that selectively target D4R may also be administered to a subject before acquired working memory deficit occurs. According to the need, a pharmaceutical composition comprising a therapeutically effective amount of one or more compounds that selectively target D4R may also be administered to a subject while acquired working memory deficit is occurring. In some embodiments of the present invention, the treatment may include enhancing or improving working memory or associated memory, and/or cognitive flexibility.

Embodiments of the present invention provide pharmaceutical compositions wherein each pharmaceutical composition comprises a therapeutically effective amount of one or more respective selective dopamine D4 receptor agonists and/or pharmaceutically acceptable analogs, salts or hydrates of the one or more respective selective dopamine D4 receptor agonists as an active ingredient in a formulation. When the pharmaceutical composition is administered to a subject, the pharmaceutical may improve the subject's working memory.

A pharmaceutical composition that comprises a therapeutically effective amount of one or more respective selective dopamine D4 receptor agonists and/or pharmaceutically acceptable analogs, salts or hydrates of the one or more respective selective dopamine D4 receptor agonists may be administered to a subject with a pharmaceutical carrier or a nutraceutical carrier.

In some embodiments of the present invention, the one or more respective selective dopamine D4 receptor agonists comprise PD 168077, the structure of which is shown in FIG. 1 and of which the IUPAC name is N-([4-(2-cyanophenyl)piperazin-1-yl]methyl)-3-methylbenzamide. In some embodiments of the present invention, the one or more respective selective dopamine D4 receptor agonists may also comprise pharmaceutically acceptable analogs, salts or hydrates of PD 168077.

Figure 2:
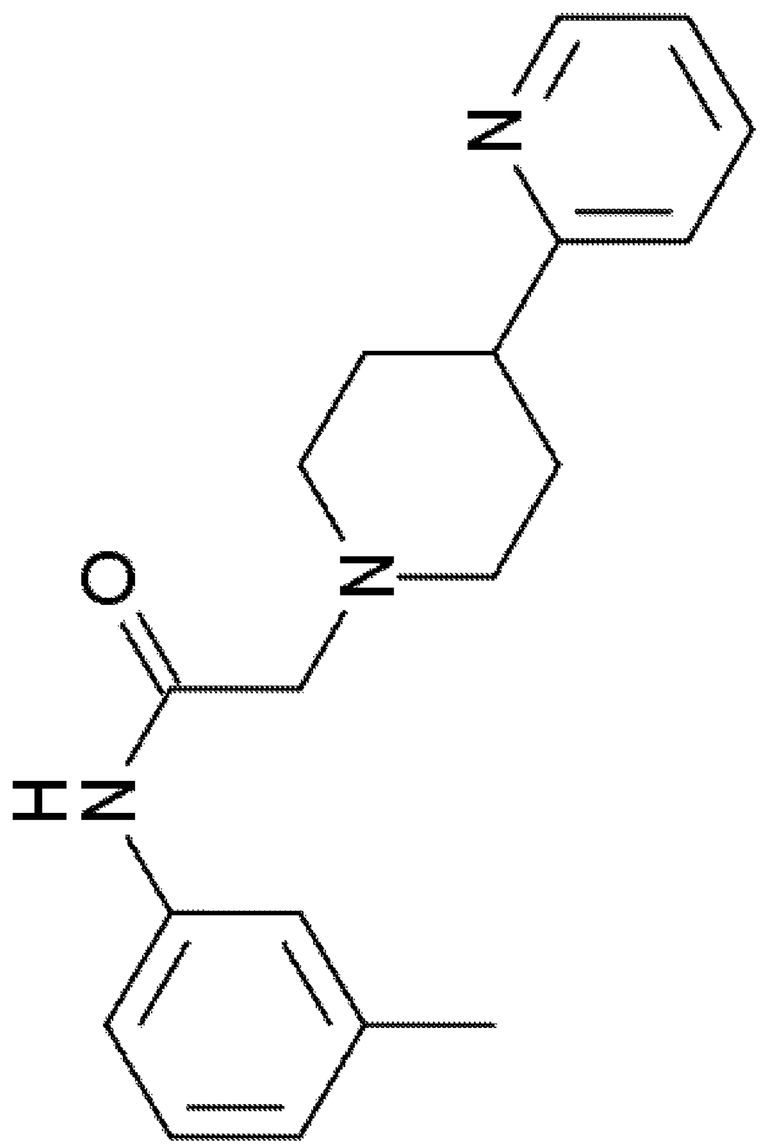
FIG. 2 shows the structure of a selective D4 receptor agonist A-412997.

Some other embodiments of the present invention provide that the one or more respective selective dopamine D4 receptor agonists comprise A-412997, of which structure is shown in FIG. 2 and of which the IUPAC name is N-(3-methylphenyl)-2-(4-pyridin-2-ylpiperidin-1-yl)acetamide. In some embodiments of the present invention, the one or more respective selective dopamine D4 receptor agonists may also comprise pharmaceutically acceptable analogs, salts or hydrates of A-412997.

According to some embodiments of the present invention, the one or more respective selective dopamine D4 receptor agonists and/or pharmaceutically acceptable analogs, salts or hydrates of the one or more respective selective dopamine D4 receptor agonists are administered to a subject at a dosage depending on the subject's body weight. For example, PD 168077 at an amount of about 10 mg per kilogram of subject body weight shows improvement in working memory in prenatal nicotine exposure mouse models. PD 168077 at an amount of about 20 mg per kilogram of subject body weight shows greater improvement in working memory in prenatal nicotine exposure mouse models. According to particular circumstance surrounding each situation, PD 168077 and/or pharmaceutically acceptable analogs, salts or hydrates of PD 168077 may also be administered to a subject in a dose less than about 10 mg, between about 10 mg to about 15 mg, and more than about 20 mg per kilogram of subject body weight.

Accordingly, the therapeutically effective amount of one or more respective selective dopamine D4 receptor agonists and/or pharmaceutically acceptable analogs, salts or hydrates of the one or more respective selective dopamine D4 receptor agonists may be flexible in a wide variety with regard to a specific compound that selectively targets dopamine D4 receptor and with regard to the subject. The dose of one or more respective selective dopamine D4 receptor agonists and/or pharmaceutically acceptable analogs, salts or hydrates of the one or more respective selective dopamine D4 receptor agonists, according to the need of a subject, may be less than 10 mg, about 10 mg, between about 10 mg to about 15 mg, about 15 mg, between about 15 mg to about 20 mg, about 20 mg, or more than 20 mg per kilogram of subject body weight, respectively. The dose of one or more respective selective dopamine D4 receptor agonists and/or pharmaceutically acceptable analogs, salts or hydrates of the one or more respective selective dopamine D4 receptor agonists may also be determined by one skilled in the art. For example a dosage regimen may be determined based on the situation of a subject having a need thereof.

According to embodiments of the present invention, a pharmaceutical composition, such as a pill or liquid, etc., comprising at least one pharmaceutically effective dose unit of a composition that comprises one or more respective selective dopamine D4 receptor agonists and/or pharmaceutically acceptable analogs, salts or hydrates of one or more respective selective dopamine D4 receptor agonists may be developed for improving memory. Such product may be a pharmaceutical composition which comprises one or more respective compounds selectively target dopamine D4 receptor, such as one or more respective selective dopamine D4 receptor agonists, and one or more respective pharmaceutically acceptable vehicle or a nutraceutical carrier with which the one or more respective compounds are administered to a subject.

The present invention is further defined in the following examples, in which all parts and percentages are by weight and degrees are Celsius, unless otherwise stated. It should be understood that these examples are given by way of illustration only. From the above discussion and these examples, one skilled in the art may ascertain the essential characteristics of embodiments of the present invention. Without departing from the spirit and scope thereof, one skilled in the art may make various changes and modifications of the invention to adapt it to various usages and conditions. All publications, including patents and non-patent literature, referred to in this specification are expressly incorporated by reference herein.

EXAMPLES

Example 1

Development of a Prenatal Nicotine Exposure Mouse Model

Maternal smoking during pregnancy is associated with increased risk for ADHD and associated cognitive impairment in the exposed offspring. Consistent with these findings, preclinical animal models show that prenatal nicotine exposure (PNE) produces hyperactivity, cognitive deficits and impaired dopamine receptor function in the prefrontal cortex. As discussed above, prefrontal cortical dopamine plays an important role in working memory, learning and attention.

A prenatal nicotine exposure (PNE) mouse model to screen for drugs that alleviate the symptoms of ADHD and associated working memory deficits is developed.[13,14] In this model, adult female C57/B6 mice are exposed to nicotine (100 μg/ml nicotine and 2% saccharin in drinking water, pH 7.2) starting 4-6 weeks prior to mating with drug-naïve male mice, and throughout their pregnancies. Two groups of age- and bodyweight-matched female mice are used as controls. In the saccharin-only (SAC) control group, mice were exposed to saccharin alone (2% saccharin in drinking water, pH 7.2), and mice in the plain drinking water (WATER) control group were exposed to drinking water without any additives. On the day the mice littered, the litter size was standardized to contain 6-8 offspring (4 males and 4 females, whenever possible). Within 48 hours of birth offspring from the PNE, SAC and WATER groups were removed from their biological mothers and cross fostered to drug-naïve nursing dams. At the age of 90 days (postnatal day 90; P90), male offspring from each group were used in experimental analyses.

Example 2

Tests of Changes in Working Memory in the PNE Mouse Model

Figure 3:
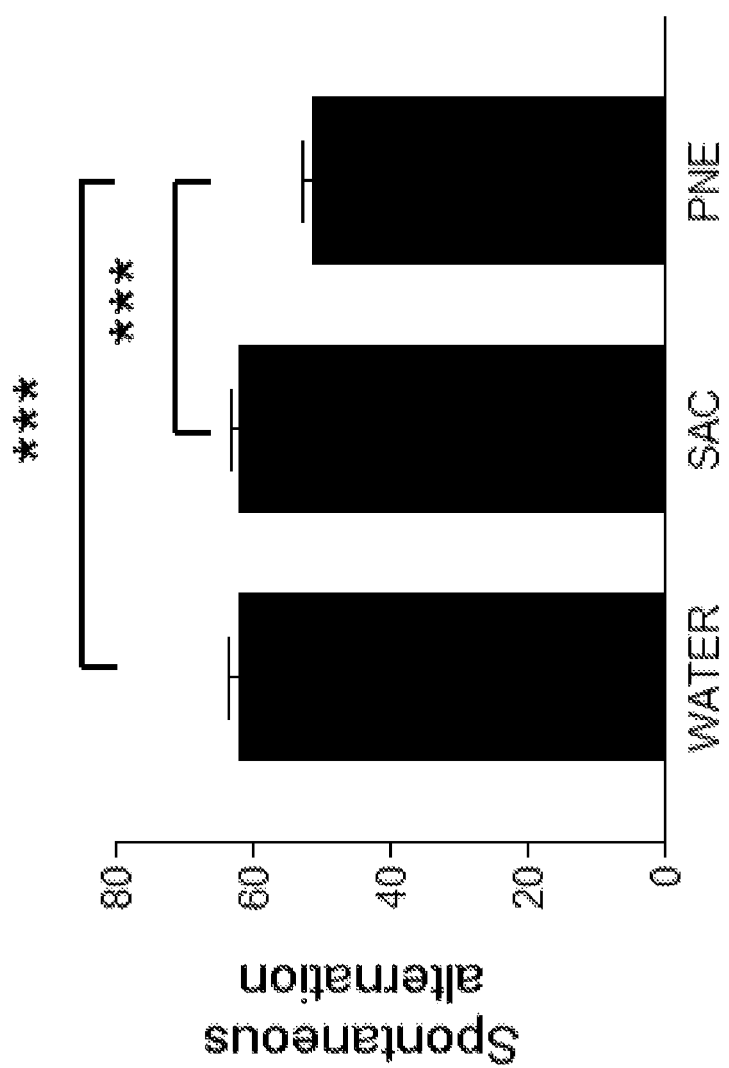
FIG. 3 is a graph showing reduction of spontaneous alternation in a Y-maze assay in mice from the prenatal nicotine exposure (PNE) group.

On postnatal day 90 (P90), a Y-maze assay is used to examine changes in spontaneous alternation in the PNE mouse model. Spontaneous alternation is a widely accepted measure of spatial working memory in rodents.[15,16] As shown in FIG. 3, male mice from the PNE group show significant reductions in spontaneous alternation in a Y-maze assay compared to control groups (WATER and SAC) (Mean±SEM, PNE vs. SAC: 49.0±3.4 vs. 60.0±3.1, $P<0.05$). There are no significant differences between the SAC and WATER groups, indicating that saccharin alone had no significant effect. Mean±SEM values are shown, n=12 per group. One-way ANOVA, $F_{(2,35)}=14.67$, $p<0.001$. Tukey's Multiple Comparison Test, ***$P<0.001$.

Following the Y maze assay, $GTP_{\gamma}S$ receptor binding assay is performed to examine the dopamine receptor signaling in mice of different groups and therefore to determine which dopamine subtypes are activated. $GTP_{\gamma}S$ binding assay is used to measure agonist-induced dopamine receptor-G-protein coupling in membrane preparations obtained from specific brain regions such as the frontal cortex.[17] This assay uses pharmacological compounds that selectively activate each receptor subtype. Since compounds selective for each of the 5 dopamine receptor subtypes are not available yet, testing is limited to assaying activities of the D2/D3 and D4 receptor only. In this assay, a D2 receptor agonist LY 171555 and a selective D4R agonist PD 168077, both in 30 μM, are used to exam the activities of D2/D3 receptor and D4 receptor, respectively.

Figure 4:
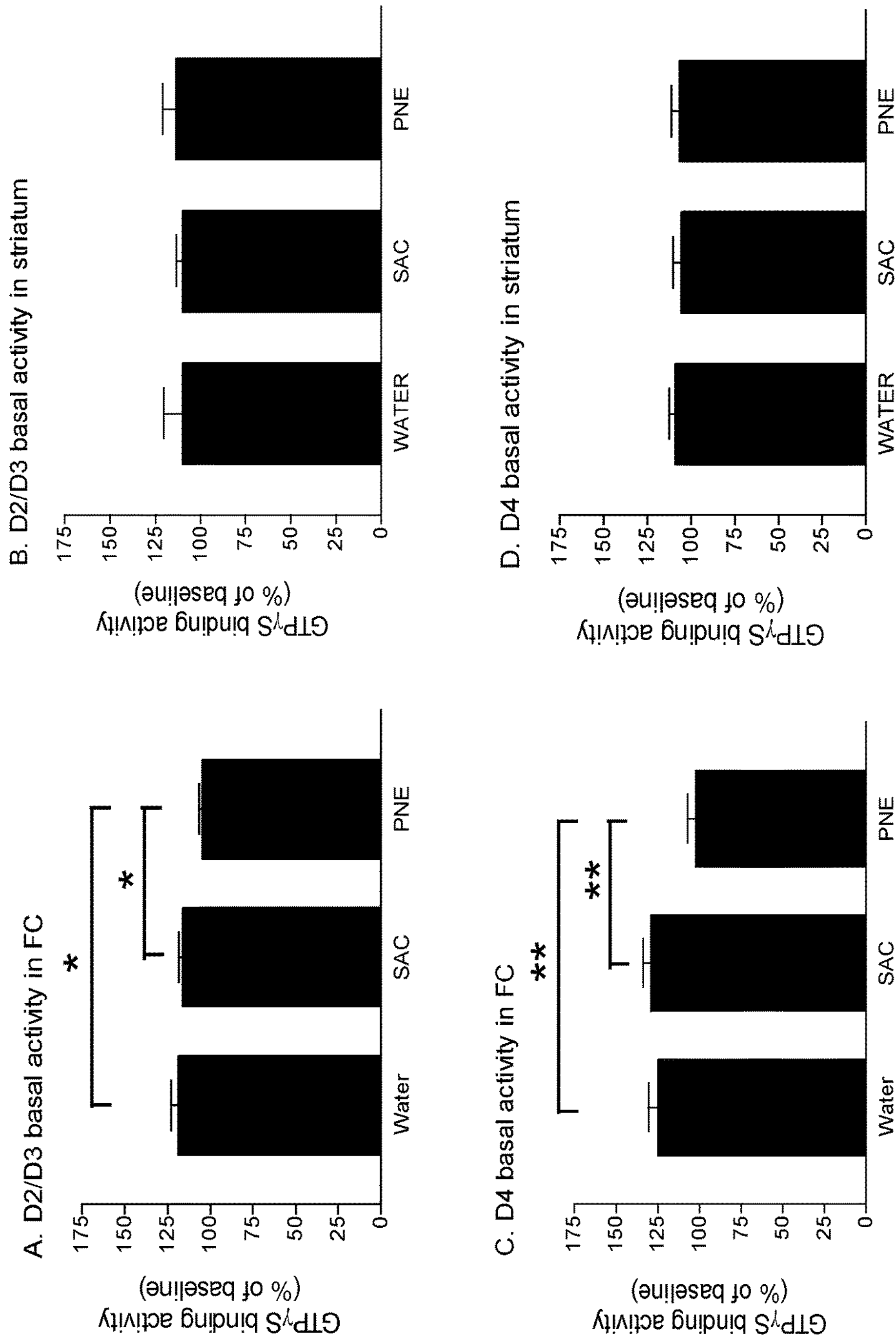
FIG. 4 is a set of graphs showing the reductions in dopamine D2/D3 and D4 receptor activities in the frontal cortex of PNE mice.

As shown in FIG. 4, compared to SAC or WATER mice, the activity of dopamine D2/D3 receptors (Panel A of FIG. 4) and the activity of dopamine D4 receptors (Panel C of FIG. 4) in the frontal cortex (FC) are both significantly reduced in PNE mice. For example, the activity of D2/D3 receptors in PNE mice vs. the activity of D2/D3 receptors in SAC mice is about 94.0±5.0 vs. 110.9±5.4, $P<0.05$; the activity of D4 receptors in PNE mice vs. the activity of D4 receptors in SAC mice is about 92.4±6.1 vs. about 124.6±6.5, $P<0.01$. However, the activities of dopamine D2/D3 receptors (Panel B of FIG. 4) and dopamine D4 receptors (Panel D of FIG. 4) in striatum are not significantly reduced in PNE mice. D2/D3 in FC: $F_{(2,23)}=6.556$, $p<0.01$; D4 in FC: $F_{(2,35)}=7.023$, $p<0.01$. Mean±SEM, Tukey's Multiple Comparison Test, *$p<0.05$, **$P<0.01$.

Example 3

Administration of Selective D4R Agonist but not Selective D1 or D2/D3 Agonist Increases Spontaneous Alternations in the PNE Mice In additional experiments, saline, selective D1 receptor agonist (A-77636), selective D2/D3 receptor agonist (LY 171555), and selective D4 receptor agonist (PD 168077) are administered to the PNE and SAC mice followed with the assay of spontaneous alternations using the Y-maze. The selective D1 receptor agonist used here is not suitable for the GTPγS binding assay used in the experiments reported in FIG. 4.

Figure 5:
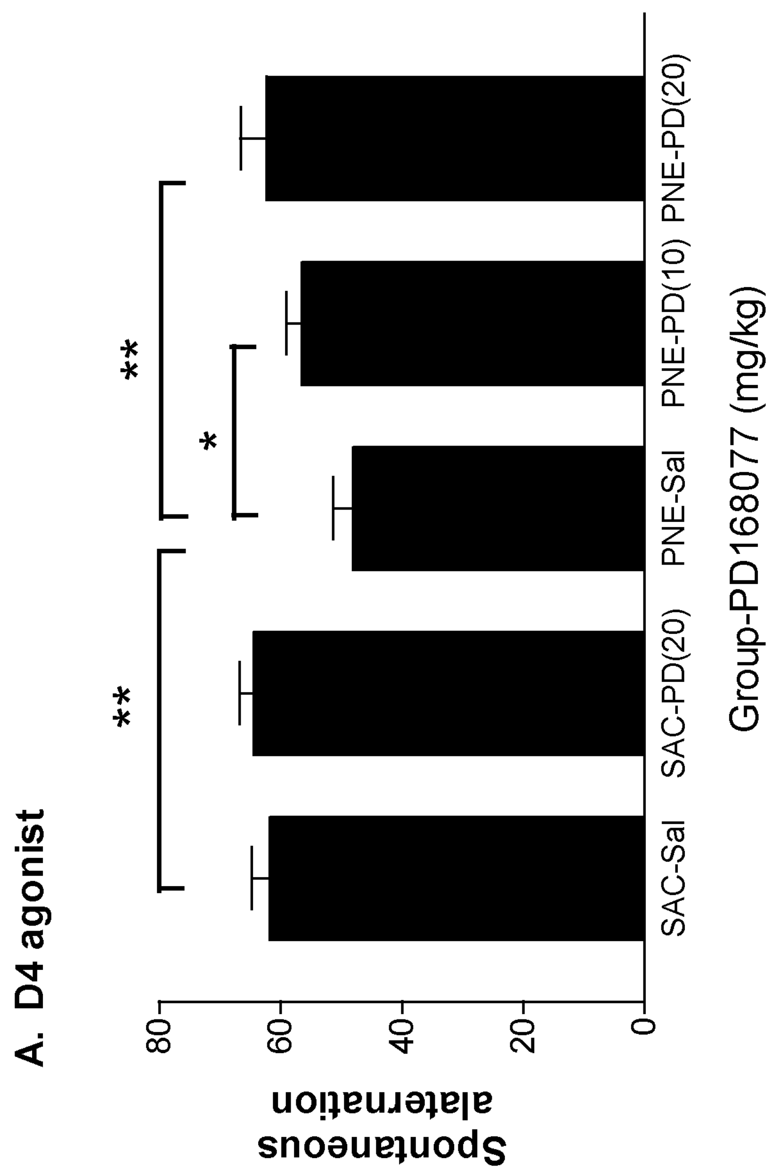
FIG. 5 is a graph showing the effect of a selective D4 agonist, PD 168077, on increasing spontaneous alternations in the PNE mice.

FIG. 5 shows that the selective D4 receptor agonist PD 168077 produces improvement in spontaneous alternations in the PNE mice in a dose dependent manner. As the dose increases from about 10 mg/kg to about 20 mg/kg, the improvement in spontaneous alternations is greater. Although at a dose of 20 mg/kg, the selective D4 receptor agonist PD 168077 produces some changes in spontaneous alternations in the SAC group, the change is not significant ($F_{(3,31)}=9.129$, $P<0.001$). After administration of the selective D4R agonist PD 168077, there is no statistically significant difference in spontaneous alternations between the PNE group and the SAC group of mice. This is a demonstration that administration the selective D4R agonist may treat deficit in spontaneous alternations in the PNE mice.

In other experiments, the effects of selective D1 receptor agonist A-77636 and selective D2/D3 receptor agonist LY 171555 are tested. To minimize animal use, these experiments only use the PNE mice, which is the only group of mice showing deficits in spontaneous alternations. The results show that neither the D1 nor the D2/D3 agonist produces significant changes in spontaneous alternations (Panel A and Panel B of FIG. 6). Mean±SEM, N=8-9, *$P<0.05$, **$P<0.01$.

Figure 6:
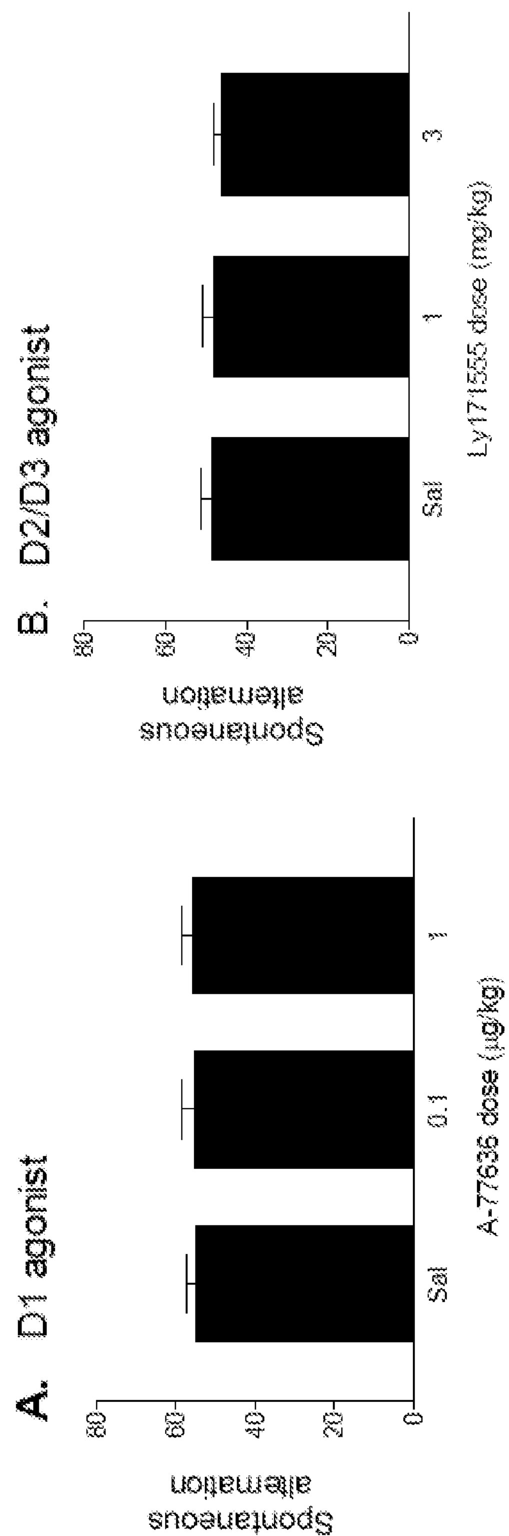
FIG. 6 is a set of graphs showing the effect of selective D1 and D2/D3 agonists on increasing spontaneous alternations in the PNE mice.

The data in FIGS. 4, 5 and 6 show that reduced activity of the D4 receptor is associated with decreased spontaneous alternations in the PNE mice and that activation of the D4 receptor using a selective agonist abrogates the deficits. Moreover, the D4 receptor agonist at the doses used here does not produce significant changes in the control groups of mice. It is therefore concluded that selective D4 receptor agonist PD 168077 may be used as pharmacological therapy for the treatment of working memory deficits.

Example 5

Figure 7:
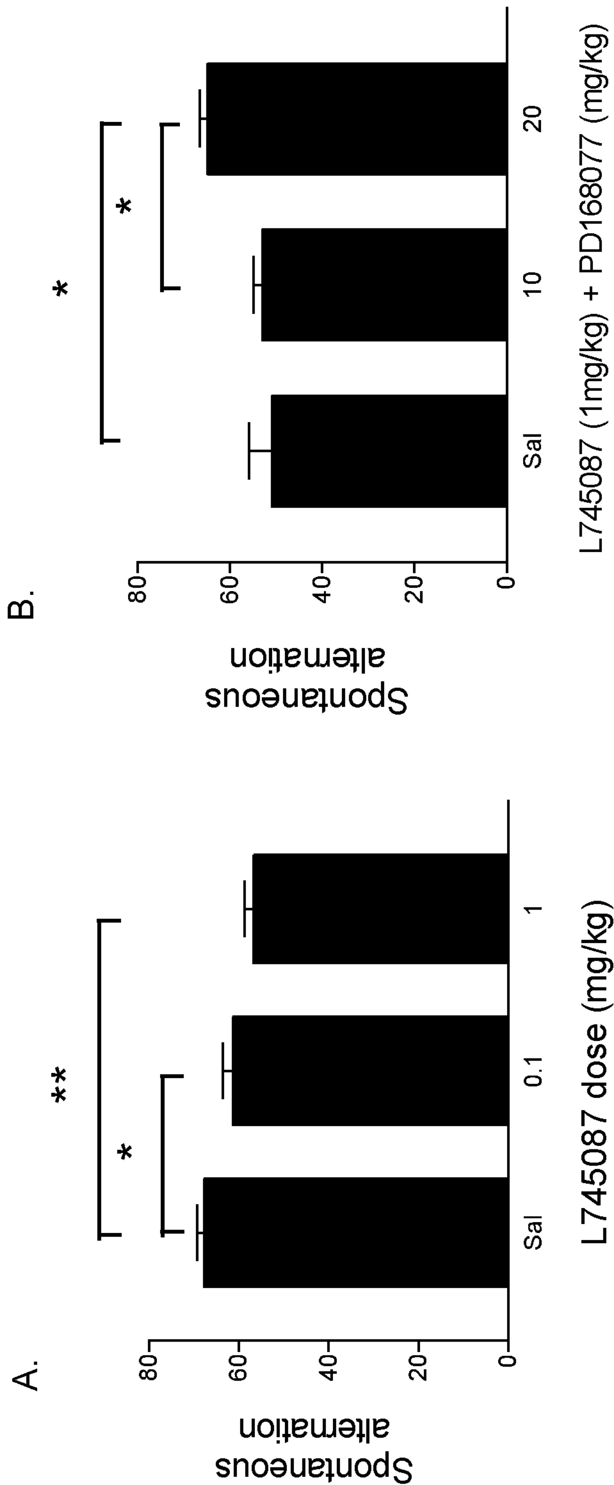
FIG. 7 is a set of graphs showing the effect of PD 168077 on abolishment of a spontaneous alternation reduction induced by a D4 receptor antagonist, L 745087.

Pharmacological Blockade of the D4R in Drug Naïve Mice Decreases Spontaneous Alternations To ascertain unequivocally whether the dopamine D4 receptor plays essential roles in working memory function, spontaneous alternations in the Y-maze in drug naïve mice, i.e., WATER group mice, are tested by pharmacological blockade of the D4 receptor using the selective D4 receptor antagonist L 745087. As shown in Panel A of FIG. 7, at a dose of 0.1 mg/kg selective D4 receptor antagonist L 745087 reduces spontaneous alternation in drug naïve mice. As the dose increases to 1 mg/kg, the spontaneous alternation decrease significantly ($F_{(2,29)}=9.001$, $P<0.01$) (Panel A, FIG. 7). Selective D4 receptor antagonist L 745087 causes a dose-dependent decrease in spontaneous alternation (Panel A of FIG. 7). Panel B of FIG. 7 shows that decrease was abrogated by the selective D4 agonist, PD 168077. ($F_{(2,17)}=4.48$ $P<0.05$). Mean±SEM, n=6-10 per group. Tukey's Multiple Comparison Test, *$P<0.05$, $P<0.01$. The administration of the selective D4 receptor agonist PD 168077 abolishes the antagonist-induced decreases in spontaneous alternations in a dose-dependent manner (Panel B of FIG. 7**). These data establish the essential role of the D4 receptor in working memory function. The data also demonstrate that decreased function of the D4 receptor is associated with working memory deficits independent of PNE.

Example 6

Methylphenidate Improves Spontaneous Alternation in PNE Mice

Methylphenidate, the classic stimulant treatment for ADHD, is examined for its efficacy in alleviating working memory deficits in the PNE mice. It is disclosed that methylphenidate increases extracellular dopamine in the frontal cortex of mice.[1,14] In the example of the present invention, saline or a therapeutic equivalent dose of methylphenidate[18] is administered to PNE and SAC mice. The PNE and SAC mice administered saline or a therapeutic equivalent dose of methylphenidate are assayed for spontaneous alternations in the Y-maze.

Figure 8:
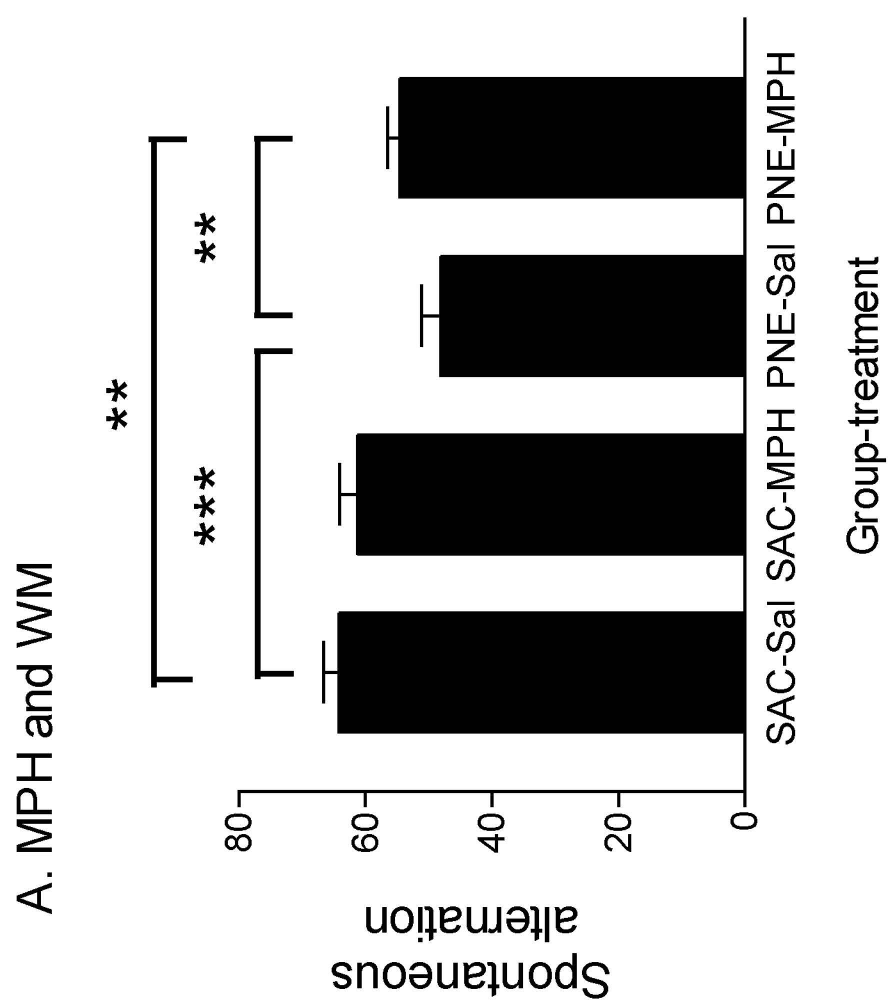
FIG. 8 is a graph showing the effect of methylphenidate (MPH) on improvement of spontaneous alternation in PNE mice.

In this example, a single oral administration of methylphenidate at a dose 0.75 mg/kg and at about 30 minutes before the Y maze assay reverses the deficits in alternation. As shown in FIG. 8, Saline vs. MPH is equivalent to about 48.0±2.2 vs. about 57.1±1.8, $P<0.05$. Methylphenidate increases spontaneous alternations in the PNE mice but has no significant effect in the SAC control group ($F_{(3,35)}=32.06$, $P<0.0001$). The methylphenidate-induced increase in spontaneous alternations in the PNE mice is such that there is no longer a significant difference between the methylphenidate-exposed PNE mice and saline-exposed SAC control mice (FIG. 8).

Figure 9:
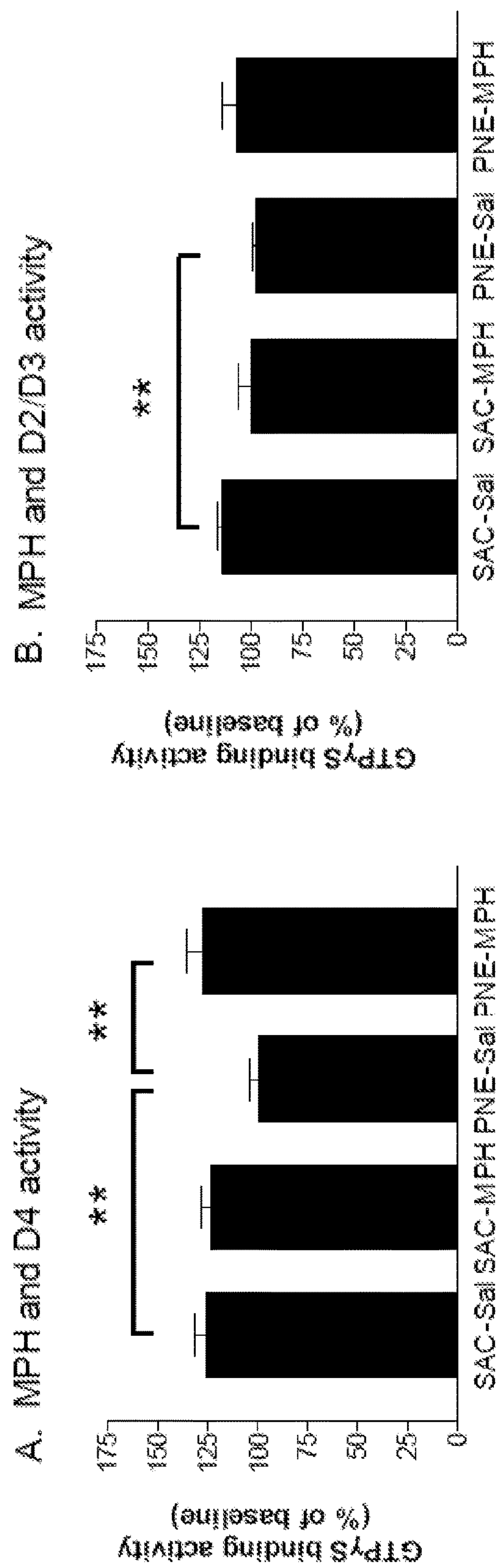
FIG. 9 is a set of graphs showing the effect of methylphenidate (MPH) on increase the dopamine D4 receptor activity in comparison the effect of MPH on increase the dopamine D2/D3 receptor activity.

D2/D3 and D4 receptor activities are also analyzed using $GTP_{\gamma}S$ binding assays with frontal cortical membrane preparations from PNE and SAC mice following the methylphenidate treatment. Increases are found in D4 agonist-induced G-protein coupling in the frontal cortices of PNE mice following the methylphenidate treatment, compared to saline treatment (Panel A, FIG. 9). The activity of D4 receptor in the prefrontal cortex of saline treated PNE mice vs. the activity of D4 receptor in the prefrontal cortex of MPH treated PNE mice is equivalent to about 92.0±3.5 vs. about 131.6±11.6, $P<0.05$. However, as shown in Panel B of FIG. 9, there is no significant change in D4 receptor activity in the SAC group receiving the methylphenidate treatment. The MPH administration does not significantly affect D2/3 activity. In addition, the methylphenidate treatment also does not produce significant alterations in D2/D3 receptor coupling to G-protein in the frontal cortices of the PNE or SAC mice. Accordingly, methylphenidate increased frontal cortical D4 receptor activity ($F_{(3,39)}=10.14$, $P<0.0001$), but not D2/D3 receptor activity in the PNE mice ($F_{(3,39)}=10.13$, $p<0.0001$) (Panel A and Panel B, FIG. 9). Mean±SEM, n=10-11 per group. Tukey's without producing significant effects in the SAC group Multiple Comparison Test, $p<0.01$, $*P<0.001$.

These above data show that PNE produces significant deficits in working memory, and prefrontal cortical D2/3 and D4 receptor activity. Since MPH treatment reverses the Y-maze deficits and D4 receptor activity but not D2/3 activity, it is suggested that the deficits in working memory in the PNE mouse model are associated with reduced prefrontal cortical D4 receptor activity.

It is believed that the improvement in spontaneous alternations produced by methylphenidate in the PNE mice was associated with specific and significant increases in D4 receptor activity but not D2/D3 receptor activity. Although methylphenidate causes the increases in frontal cortical dopamine level, the improvement of working memory in the PNE mice is associated specifically with increased D4 receptor activity.

Example 7

Comparison of the Effect of Methylphenidate with the Effect of the Selective D4R Agonist The effect of methylphenidate and the effect of PD 168077 on spontaneous alternation in the PNE mice are compared. Since PD 168077 selectively targets the D4 receptor, it is predicted that this drug would be more effective.

Figure 10:
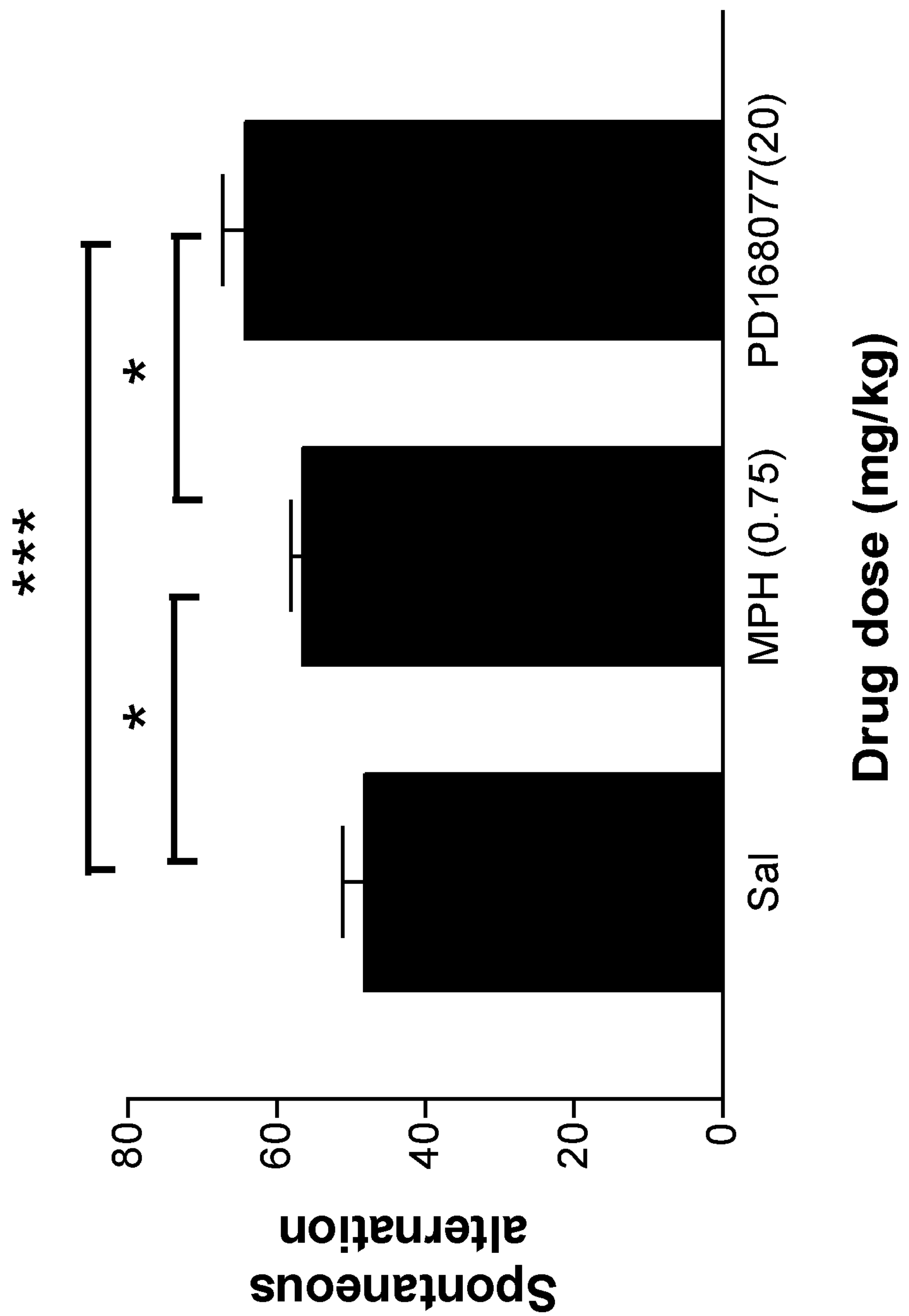
FIG. 10 is a graph showing a comparison of the effects of MPH and the selective D4 receptor agonist PD 168077 on spontaneous alternations in the PNE mice.

As shown in FIG. 10, although both the compounds increase spontaneous alternations, the effect of PD 168077 is greater than that of MPH: $F_{(2,26)}=17.6$, $p<0.0001$, n=9-10 per group, $*p<0.05$, $***p<0.001$. This comparison shows that PD 168077, compared to methylphenidate, produces greater improvements in working memory in the PNE mice.

It is therefore suggested that compounds that selectively activate the D4 receptor are a class of drugs for the treatment of working memory deficits and/or other kinds of memory deficits.

Example 8

Examples of Uses Utilities

A composition that comprises a therapeutically effective amount of one or more respective selective dopamine D4 receptor agonists and/or pharmaceutically acceptable analogs, salts or hydrates of the one or more respective selective dopamine D4 receptor agonists is used for the treatment of working memory deficits.

A composition that comprises a therapeutically effective amount of one or more respective selective dopamine D4 receptor agonists and/or pharmaceutically acceptable analogs, salts or hydrates of the one or more respective selective dopamine D4 receptor agonists is used for the prevention of working memory deficits.

A composition that comprises a therapeutically effective amount of one or more respective selective dopamine D4 receptor agonists and/or pharmaceutically acceptable analogs, salts or hydrates of the one or more respective selective dopamine D4 receptor agonists is used for the enhancement working memory.

A composition that comprises a therapeutically effective amount of one or more respective selective dopamine D4 receptor agonists and/or pharmaceutically acceptable analogs, salts or hydrates of the one or more respective selective dopamine D4 receptor agonists as an active ingredient in a formulation to improve working memory of a subject. Such composition may also be used for the prevention of cognitive flexibility or other executive function deficits.

A composition that comprises a therapeutically effective amount of one or more respective selective dopamine D4 receptor agonists and/or pharmaceutically acceptable analogs, salts or hydrates of the one or more respective selective dopamine D4 receptor agonists is used for the treatment of cognitive flexibility deficits or related conditions.

A composition that comprises a therapeutically effective amount of one or more respective selective dopamine D4 receptor agonists and/or pharmaceutically acceptable analogs, salts or hydrates of the one or more respective selective dopamine D4 receptor agonists is used for the enhancement of cognitive flexibility.

Examples of Routes of Administration

A composition is prepared that comprises a therapeutically effective amount of one or more respective selective dopamine D4 receptor agonists and/or pharmaceutically acceptable analogs, salts or hydrates of the one or more respective selective dopamine D4 receptor agonists may be administered by a variety of routes. In effecting treatment of a subject afflicted with disorders described herein, that contain working memory deficits, the composition may be administered in any form or mode that makes the composition bioavailable in an effective amount. The routes encompass oral and parenteral routes. For example, the compounds may be administered orally, by inhalation, or by the subcutaneous, intramuscular, intravenous, transdermal, intranasal, rectal, ocular, topical, sublingual, buccal, or other routes.

One skilled in the art of preparing formulations may readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)).

Pharmaceutical Compositions

The pharmaceutical compositions that comprise therapeutically effective amount of one or more respective selective dopamine D4 receptor agonists or pharmaceutically acceptable analogs, salts or hydrates of the one or more respective selective dopamine D4 receptor agonists are prepared in a manner well known in the pharmaceutical art. The carrier or excipient may be a solid, semi-solid, or liquid material that may serve as a vehicle or medium for the active ingredient. Suitable carriers or excipients are well known in the art. The pharmaceutical composition may be adapted for oral, inhalation, parenteral, or topical use and may be administered to the subject in the form of tablets, capsules, powders, granules, delayed release capsules, syrups, aerosols, inhalants, suppositories, solutions, suspensions, catheters containing the composition, syringes containing the composition, implants containing the composition, or the like.

Pharmaceutical compositions of the present invention that comprise a therapeutically effective amount of one or more respective selective dopamine D4 receptor agonists and/or pharmaceutically acceptable analogs, salts or hydrates of the one or more respective selective dopamine D4 receptor agonists may be administered orally, for example, with an inert diluent or capsules or compressed into tablets. For the purpose of oral therapeutic administration, the compounds may be incorporated with excipients and used in the form of tablets, troches, capsules, powder, elixirs, suspensions, syrups, wafers, chewing gums and the like. The pharmaceutical compositions may also be in forms such as tablet, a powder, a pill, a granule, a capsule, a solution, a sugar-coated tablet, a syrup, a catheter containing the composition, and a syringe containing the composition.

In some embodiments of the present invention, the particular selective dopamine D4 receptor agonists and/or pharmaceutically acceptable analogs, salts or hydrates of the particular selective dopamine D4 receptor agonists used in such pharmaceutical compositions may be varied depending upon the particular form of the composition. The amount of the dopamine D4 receptor agonist(s), salt(s) and/or hydrate(s) present in a composition is such that a suitable dosage may be obtained. Preferred compositions and preparations according to the present invention may be determined by a person skilled in the art.

In one embodiment of the present, active ingredients in the product comprising the one or more respective selective dopamine D4 receptor agonists and/or pharmaceutically acceptable analogs, salts or hydrates of the one or more respective selective dopamine D4 receptor agonists may be in delayed released form such as delayed release capsules or delayed release tablets, etc.

The pharmaceutical composition in one embodiment of the present invention comprises a therapeutically effective amount of A-412997 and/or pharmaceutically acceptable analogs, salts or hydrates of A-412997.

The pharmaceutical composition in one embodiment of the present invention comprises a therapeutically effective amount of PD 168077 and/or pharmaceutically acceptable analogs, salts or hydrates of PD 168077.

Doses

The compounds of various embodiments of the present invention may be used alone at appropriate dosages defined by routine testing in order to obtain optimal pharmacological effect, while minimizing any potential toxic or otherwise unwanted effects.

An effective amount may be determined by the attending diagnostician, as one skilled in the art, by the use of conventional techniques and by observing results obtained under analogous circumstances. In determining an effective amount, the dose of a compound, a number of factors are considered by the attending diagnostician, including, but not limited to: the compound to be administered; the species of mammal; the size, age, and general health of the subject; the specific disorder involved; the degree of involvement or the severity of the disorder; the response of the individual subject; the mode of administration; the bioavailability characteristics of the preparation administered; the dose regimen selected; the use of other concomitant medication; and other relevant circumstances.

The specific dose administered may be determined by the particular circumstances surrounding each situation. These circumstances may include: the route of administration, the prior medical history of the subject, the symptom being treated, the severity of the symptom being treated, and the age of the subject. The subject's attending physician should determine the therapeutic dose administered in light of the relevant circumstances.

Also, it is to be understood that the exact dose may be determined, in accordance with the standard practice in the medical arts of "dose titrating" the subject; that is, initially administering a low dose of the compound, and gradually increasing the dose until the desired therapeutic effect is observed.

It is to be further understood that the dosage regimen may be selected in accordance with a variety of factors. These include type, species, age, weight, sex and medical condition of the subject; the severity of the condition to be treated; the route of administration; the kidney and liver functions of the subject; and the particular compounds employed. A physician of ordinary skill may readily determine and prescribe the effective amount of the drug required to prevent, counter or arrest the progress of the disease or disorder that is being treated.

In one embodiment, a selective D4R agonist employed in the methods described herein may be administered in doses of about 10 mg/kg, 15 mg/kg, or 20 mg/kg body weight. In an embodiment, a selective D4R agonist employed in the methods described herein may be administered in a dose of between about 10 mg/kg to about 15 mg/kg body weight. In one embodiment, a selective D4R agonist employed in the methods described herein may be administered in a dose of less than 10 mg/kg body weight. According to the embodiment of the present invention, a selective D4R agonist employed in the methods described herein may be administered at a dose of more than 20 mg/kg body weight.

In addition, the compounds may be used as adjunctive therapy with known drugs to reduce the dosage required of these traditional drugs, and thereby reduce their side effects.

In one embodiment, the present invention provides a product, such as a kit, etc., comprising at least one pharmaceutically effective dosage unit of a composition that comprises a therapeutically effective amount of one or more respective selective dopamine D4 receptor agonists and/or pharmaceutically acceptable analogs, salts or hydrates of the one or more respective selective dopamine D4 receptor agonists for administration to a subject to improve working memory.

In one embodiment of the present invention, this product may be used for administration according to a continuous schedule having a dosing interval selected from one or more of: once daily dosing and/or multiple daily dosing.

Although an example of a selective D4R agonist PD 168077 is shown for treating working memory deficit in PNE mice, it will be appreciated that other members of the class of selective D4R agonists may be used for the treatment of working memory deficits. The subject receiving such treatment is not limited to PNE mice. Working memory deficits are also not limited to be induced by prenatal nicotine exposure. It could be due to any reason, including those unknown.

It is intended that the invention not be limited to the particular embodiment disclosed herein contemplated for carrying out this invention, but that the invention will include all embodiments falling within the scope of the claims.

All documents, patents, journal articles and other materials cited in the present application are incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:

1. Goldman-Rakic P S (1995) Cellular basis of working memory. Neuron 14:477-485.
2. Goldman-Rakic P S (1996) Regional and cellular fractionation of working memory. Proc Natl Acad Sci USA 93:13473-13480.
3. Goldman-Rakic P S (1999) The "psychic" neuron of the cerebral cortex. Ann N Y Acad Sci 868:13-26.
4. Park S, Holzman P S, Goldman-Rakic P S (1995) Spatial working memory deficits in the relatives of schizophrenic patients. Arch Gen Psychiatry 52:821-828.
5. Arnsten A F (2011) Prefrontal cortical network connections: key site of vulnerability in stress and schizophrenia. Int J Dev Neurosci 29:215-223.
6. Wang M, Gamo N J, Yang Y, Jin L E, Wang X J, Laubach M, Mazer J A, Lee D, Arnsten A F (2011) Neuronal basis of age-related working memory decline. Nature 476:210-213.
7. Alderson R M, Kasper L J, Hudec K L, Patros C H (2013) Attention-deficit/hyperactivity disorder (ADHD) and working memory in adults: a meta-analytic review. Neuropsychology 27:287-302.
8. Zhang K, Grady C J, Tsapakis E M, Andersen S L, Tarazi F I, Baldessarini R J (2004) Regulation of working memory by dopamine D4 receptor in rats. Neuropsychopharmacology 29:1648-1655.
9. Robbins T W, Arnsten A F (2009) The neuropsychopharmacology of fronto-executive function: monoaminergic modulation. Annu Rev Neurosci 32:267-287.
10. Faraone S V, Biederman J (1998) Neurobiology of attention-deficit hyperactivity disorder. Biol Psychiatry 44:951-958.
11. Lasky-Su J, Lange C, Biederman J, Tsuang M, Doyle A E, Smoller J W, Laird N, Faraone S (2008) Family-based association analysis of a statistically derived quantitative traits for ADHD reveal an association in DRD4 with inattentive symptoms in ADHD individuals. Am J Med Genet B Neuropsychiatr Genet 147B:100-106.
12. Monuteaux M C, Seidman L J, Faraone S V, Makris N, Spencer T, Valera E, Brown A, Bush G, Doyle A E, Hughes S, Helliesen M, Mick E, Biederman J (2008) A preliminary study of dopamine D4 receptor genotype and structural brain alterations in adults with ADHD. Am J Med Genet B Neuropsychiatr Genet 147B:1436-1441.
13. Zhu J, Lee K P, Spencer T J, Biederman J, Bhide P G (2014) Transgenerational transmission of hyperactivity in a mouse model of ADHD. J Neurosci 34:2768-2773.
14. Zhu J, Zhang X, Xu Y, Spencer T J, Biederman J, Bhide P G (2012) Prenatal nicotine exposure mouse model showing hyperactivity, reduced cingulate cortex volume, reduced dopamine turnover, and responsiveness to oral methylphenidate treatment. The Journal of neuroscience: the official journal of the Society for Neuroscience 32:9410-9418.
15. Bissonette G B, Powell E M, Roesch M R (2013) Neural structures underlying set-shifting: roles of medial prefrontal cortex and anterior cingulate cortex. Behav Brain Res 250:91-101.
16. Bissonette G B, Bae M E, Suresh T, Jaffe D E, Powell E M (2014) Prefrontal cognitive deficits in mice with altered cerebral cortical GABAergic interneurons. Behav Brain Res 259:143-151.
17. Zhu J, Spencer T J, Liu-Chen L Y, Biederman J, Bhide P G (2011) Methylphenidate and mu opioid receptor interactions: a pharmacological target for prevention of stimulant abuse. Neuropharmacology 61:283-292.
18. Balcioglu A, Ren J Q, McCarthy D, Spencer T J, Biederman J, Bhide P G (2009) Plasma and brain concentrations of oral therapeutic doses of methylphenidate and their impact on brain monoamine content in mice. Neuropharmacology 57:687-693.

What is claimed is:

1. A method comprising: administering to a subject previously identified as having a working memory deficit a composition that comprises a therapeutically effective amount of one or more respective selective dopamine D4 receptor agonists and/or pharmaceutically acceptable analogs, salts or hydrates of the respective one or more selective dopamine D4 receptor agonists to the subject to improve the working memory in the subject.

2. The method of claim 1, wherein the subject has a working memory deficit acquired before birth.

3. The method of claim 1, wherein the subject has a working memory deficit acquired after birth.

4. The method of claim 1, wherein the composition comprises a therapeutically effective amount of A-412997 and/or pharmaceutically acceptable analogs, salts or hydrates of A-412997.

5. The method of claim 1, wherein the composition comprises a therapeutically effective amount of PD 168077 and/or pharmaceutically acceptable analogs, salts or hydrates of PD 168077.

6. The method of claim 5, wherein PD 168077 and/or pharmaceutically acceptable analogs, salts or hydrates of PD 168077 are administered to the subject in a dose of less than about 10 mg per kilogram of subject body weight.

7. The method of claim 5, wherein PD 168077 and/or pharmaceutically acceptable analogs, salts or hydrates of PD 168077 are administered to the subject in a dose of about 10 mg per kilogram of subject body weight.

8. The method of claim 5, wherein PD 168077 and/or pharmaceutically acceptable analogs, salts or hydrates of PD 168077 are administered to the subject in a dose of about 15 mg per kilogram of subject body weight.

9. The method of claim 5, wherein PD 168077 and/or pharmaceutically acceptable analogs, salts or hydrates of PD 168077 are administered to the subject in a dose of about 20 mg per kilogram of subject body weight.

10. The method of claim 5, wherein PD 168077 and/or pharmaceutically acceptable analogs, salts or hydrates of PD 168077 are administered to the subject in a dose between about 10 mg to about 15 mg per kilogram of subject body weight.

11. The method of claim 5, wherein PD 168077 and/or pharmaceutically acceptable analogs, salts or hydrates of PD 168077 are administered to the subject in a dose between about 15 mg to about 20 mg per kilogram of subject body weight.

12. The method of claim 5, wherein PD 168077 and/or pharmaceutically acceptable analogs, salts or hydrates of PD 168077 are administered to the subject in a dose of more than about 20 mg per kilogram of subject body weight.

13. The method of claim 1, wherein the composition that comprises a therapeutically effective amount of one or more respective selective dopamine D4 receptor agonists and/or pharmaceutically acceptable analogs, salts or hydrates of the one or more respective selective dopamine D4 receptor agonists is administered orally.

14. The method of claim 1, wherein the composition that comprises a therapeutically effective amount of one or more respective selective dopamine D4 receptor agonists and/or one or more pharmaceutically acceptable analogs, salts or hydrates of the respective one or more selective dopamine D4 receptor agonists is administered via a parenteral route.

15. The method of claim 1, wherein the composition that comprises a therapeutically effective amount of one or more respective selective dopamine D4 receptor agonists and/or pharmaceutically acceptable analogs, salts or hydrates of the one or more respective selective dopamine D4 receptor agonists is administered with a pharmaceutical carrier.

16. The method of claim 1, wherein the composition that comprises a therapeutically effective amount of one or more respective selective dopamine D4 receptor agonists and/or pharmaceutically acceptable analogs, salts or hydrates of the one or more respective selective dopamine D4 receptor agonists is administered with a nutraceutical carrier.

* * * * *